(12) United States Patent
Wu

(10) Patent No.: US 10,443,092 B2
(45) Date of Patent: Oct. 15, 2019

(54) METHODS OF ELONGATING DNA

(71) Applicant: President and Fellows of Harvard College, Cambridge, MA (US)

(72) Inventor: Chao-ting Wu, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 382 days.

(21) Appl. No.: 14/774,291

(22) PCT Filed: Mar. 11, 2014

(86) PCT No.: PCT/US2014/023295
§ 371 (c)(1),
(2) Date: Sep. 10, 2015

(87) PCT Pub. No.: WO2014/164716
PCT Pub. Date: Oct. 9, 2014

(65) Prior Publication Data
US 2016/0032370 A1  Feb. 4, 2016

Related U.S. Application Data

(60) Provisional application No. 61/779,303, filed on Mar. 13, 2013.

(51) Int. Cl.
*C12Q 1/68* (2018.01)
*C07H 21/00* (2006.01)
*C12Q 1/6834* (2018.01)
*C12Q 1/6841* (2018.01)
*C12P 19/34* (2006.01)

(52) U.S. Cl.
CPC ............ *C12Q 1/6834* (2013.01); *C12P 19/34* (2013.01); *C12Q 1/6841* (2013.01)

(58) Field of Classification Search
CPC ................................. C12Q 1/68; C12Q 1/6869
See application file for complete search history.

(56) References Cited

U.S. PATENT DOCUMENTS

| 5,795,782 A * | 8/1998 | Church | C07K 14/705 435/4 |
| 5,851,769 A * | 12/1998 | Gray | C12Q 1/68 435/6.11 |
| 6,015,714 A * | 1/2000 | Baldarelli | C07K 14/705 435/4 |
| 6,723,513 B2 * | 4/2004 | Lexow | C12Q 1/6869 435/6.12 |
| 8,021,841 B1 * | 9/2011 | Schatz | B82Y 30/00 435/6.1 |
| 8,859,201 B2 * | 10/2014 | Goldstein | C12Q 1/6874 435/6.1 |
| 2002/0039737 A1 * | 4/2002 | Chan | B01L 3/502761 435/6.18 |
| 2002/0081744 A1 | 6/2002 | Chan et al. | |
| 2002/0182607 A1 * | 12/2002 | Subramaniam | C12Q 1/6874 435/6.12 |
| 2006/0063171 A1 * | 3/2006 | Akeson | B01L 3/502707 435/6.11 |
| 2007/0148636 A1 * | 6/2007 | Song | C12Q 1/6844 435/5 |
| 2008/0173544 A1 | 7/2008 | Seul et al. | |
| 2009/0111706 A1 | 4/2009 | Sparks et al. | |
| 2011/0201057 A1 | 8/2011 | Carr et al. | |
| 2011/0244462 A1 | 10/2011 | Bendix et al. | |
| 2013/0224736 A1 * | 8/2013 | Marie | B01L 3/502746 435/6.1 |
| 2013/0256118 A1 * | 10/2013 | Meller | B82Y 15/00 204/158.21 |
| 2016/0040220 A1 * | 2/2016 | Ceppi | C12Q 1/6827 506/2 |

FOREIGN PATENT DOCUMENTS

CA  2727850 A1  1/2005

OTHER PUBLICATIONS

Benitez et al., Microfluidic extraction, stretching and analysis of human chromosomal DNA rom single cells. Lab Chip 12(22) : 4848 (Nov. 2012).*
Allemand et al., pH-Dependent Specific Binding and Combing of DNA. Biophysical Journal 73 : 2064 (1997).*
Aston et al., Optical Mapping : An Approach for Fine Mapping. Methods in Enzymology 303 :55 (1999).*
Bauer et al.,DNA catenation maintains structure of human metaphase chromosomes. Nucleic Acids Research 40(22) :11428 (2012).*
Beliveau et al., Versatile design and synthesis platform for visualizing genomes with Oligopaint FISH probes. PNAS109(52) : 21301(2012).*
Bensimon et al., Alignment and Sensitive Detection of DNA by a Moving Interface. Science 265 : 2096(1994).*
Branton et al., The potential and challenges of nanopore sequencing. Nature Biotechnology 26(10) : 1146 (2008).*
Chan et al., DNA Mapping Using Microfluidic Stretching and Single-Molecule Detection of Fluorescent Site-Specific Tags. Genome Research 14 :1137 (2004).*
Chen et al., Nanopore sequencing of polynucleotides assisted by a rotating electric field. Applied Physics Letters 82(8) : 1308 (2003).*
Clarke et al., Continuous base identification for single-molecule nanopore DNA sequencing. Nature Nanotechnology 4 :265 (2009).*
Fransz et al., High-resolution physical mapping in *Arabidopsis thaliana* and tomato by fluorescence in situ hybridization to extended DNA fibres. The Plant Journal9(3) :421(1996).*

(Continued)

*Primary Examiner* — Ethan C Whisenant
(74) *Attorney, Agent, or Firm* — Banner & Witcoff, Ltd.

(57) ABSTRACT

The present invention relates to methods of elongating chromosomes. Embodiments of the present disclosure are directed to methods of elongating DNA by immobilizing or attaching the DNA to a substrate. According to one aspect, naturally occurring DNA includes a nucleic acid and one or more factors bound thereto, and may be referred to herein as "starting DNA".

31 Claims, 2 Drawing Sheets

(56) References Cited

OTHER PUBLICATIONS

Gueroui et al., Observation by fluorescence microscopy of transcription on single combed DNA. PNAS 99(9) : 6005 (2002).*
Heiskanen et al., Fiber-FISH : experiences and a refined protocol. Genetic Analysis :Biomolecular Engineering 12 :179 (1996).*
Henegariu et al., Rapid DNA fiber technique for size measurements of linear and circular DNA probes. BioTechniques31(2) :246(2001).*
Heng et al., High-resolution mapping of mammalian genes by in situ hybridization to free chromatin. PNAS 89 :9509(1992).*
Heng et al., Stretching DNA using the Electric Field in a Synthetic Nanopore. Naon Letters 5(10) : 1883 (2005).*
Howorka et al., Sequence-specific detection of individual DNA strands using engineered nanopores. Nature Biotechnology 19 :636 (2001).*
Herrick ert al., Single molecule analysis of DNA replication. Biochemie 81:859 (1999).*
Larson et al., Single DNA molecule stretching in sudden mixed shear and elongational microflows. Lab on a Chip 6 :1187(2006).*
Metzker, M., Sequencing Technologies—the next generation. Nature Reviews: Genetics 11 : 31 (2010).*
Parra et al., High resolution visual mapping of stretched DNA by fluorescent hybridization. Nature Genetics 5 :17 (1993).*
Perkins et al. Stretching of a single tethered polymer in a uniform flow. Science 268 :83 (1995).*
Phillips et al., Application of single molecule technology to rapidly map long DNA and study the conformation of stretched DNA Nucleic Acids Research 33(18) : 5829(2005).*
Rasmussen et al., A device for extraction, manipulation and stretching of DNA from single human chromosomes. Lab on a Chip 11 : 1431 (2011).*
Rhee et al., Nanopore sequencing technology : research trends and applications. Trends in Biotechnology 24(12) : 580 (2006).*
Strick et al.,Twisting and stretching single DNA molecules. Progress in Biophysics & molecular biology 74 : 115 (2000).*
Tegenfeldt et al., Near-field scanner for moving molecules. Physical review Letters 86(7) : 1378 (2001).*
Thomas et al., Yeast chromatin structure. FEBS Letters 66(2) : 274 (1976).*
Washizu M., DNA manipulation in electrostatic fields 7th Intl. Conf. on miniaturized cemical and biochemical analysis systems. p. 869(Oct. 2003).*
Zarkov et al., Biotechnology & Biotechnological Equipment 28(1) : 112 (2014).*
Allardet-Servent et al., Presence of one linear and one circular chromosome in Agrobacterium tumefaciens C58 genome. J. of Bacteriology 175(24) : 7869 (Year: 1993).*
Benitez et al., Microfluidic extraction, stretching and analysis of human chromosomal DNA from single cells. Lab on a Chip 12 :4848 (Year: 2012).*
Heng et al., Stretch DNA using the electric field in a synthetic nanopore. Nano Letters 5(10) : 1883 (Year: 2005).*
International Search Report issued from corresponding PCT/US2014/023295, dated Aug. 12, 2014.
Beliveau et al. "Versatile design and synthesis platform for visualizing genomes with Oligopaint FISH probes." PNAS. vol. 109, No. 52, 21301-21306.Dec. 26, 2012.

* cited by examiner

METHODS OF ELONGATING DNA

RELATED APPLICATION DATA

This application is a National Stage Application under 35 U.S.C. 371 of PCT application number PCT/US2014/023295 designating the United States and filed Mar. 11, 2014; which claims the benefit of U.S. provisional application No. 61/779,303 and filed Mar. 13, 2013 each of which are hereby incorporated by reference in their entireties.

STATEMENT OF GOVERNMENT INTERESTS

This invention was made with government support under ROI GM085169 awarded by the National Institutes of Health. The Government has certain rights in the invention.

FIELD

The present invention relates in general to methods of removing bound factors from DNA and elongating the DNA.

BACKGROUND

Methods of stretching DNA are described in K H Rasmussen, R Marie, J M Lange, W E Svendsen, A Kristensen, and K U Mir, *Lab chip,* 2011, 11:1431-44 and A device for extraction, manipulation and stretching of DNA from single human chromosomes; D L V Bauer, R Marie, K H Rasmussen, A Kristensen, K U Mir, 2012 *Nucl Acids Res,* 2012, 1-7, DNA catenation maintains structure of human metaphase chromosomes. However, additional methods of elongating DNA are desirable.

SUMMARY

Embodiments of the present disclosure are directed to methods of elongating DNA by immobilizing or attaching the DNA to a substrate. According to one aspect, naturally occurring DNA includes a nucleic acid and one or more factors bound thereto, and may be referred to herein as "starting DNA." It is to be understood that the term "DNA" is meant to include at least a nucleic acid and that aspects of the present disclosure are directed to removing factors that may be bound to the DNA. The DNA is processed by being contacted with at least one reagent, or subjected to one or more forces, which separates and/or removes the one or more factors from the nucleic acid. The bound DNA is subjected to forces sufficient to move the unbound factors away from the bound DNA. DNA where bound factors have been removed may be referred to herein as "ending DNA" or "processed DNA" or "elongated DNA." The term DNA may be used herein to refer to deoxyribonucleic acid with factors bound thereto or deoxyribonucleic acid with factors removed from or otherwise unbound from the deoxyribonucleic acid. The starting DNA is elongated as the one or more factors are removed from the starting DNA. According to one aspect, factors bound to DNA, such as naturally occurring DNA, contribute to the orientation and, therefore, length of the DNA. As factors are removed from the DNA, the DNA is no longer constrained in a particular orientation due to the one or more bound factors. Accordingly, the DNA is able to achieve an orientation determined by the nucleic acid sequence without the one or more factors that have been removed. According to one aspect, if significantly all factors have been removed, then the orientation of the DNA will be based on the nucleic acid sequence of the DNA. According to one aspect, as factors are removed from the DNA, the DNA is able to elongate from a first or starting length to a second or ending length. According to one aspect, as factors are removed from the DNA, ending DNA is elongated relative to starting DNA.

According to one aspect, the elongated DNA can be further processed by methods known to those of skill in the art such as fluorescence in situ hybridization using probes or oligopaints as described in US 2010/0304994 or DNA-paints, in situ sequencing using probes or oligopaints as described in US 2010/0304994 or DNA-paints, or amplification and sequencing methods known to those of skill in the art. In addition, the methods described herein allow one of skill to understand the sequence structure of the DNA present in a chromosome, such as whether the DNA exists as a single complete strand in a chromosome or whether the DNA exists as multiple discrete and unconnected strands. Further, nicks, gaps or breaks in the strand can be repaired using methods known to those of skill in the art prior to, during or after elongation.

According to one aspect, the elongated DNA can be processed or sequenced using nanopore sequencing technology. According to this aspect, the elongated DNA and a nanopore are placed under suitable conditions, such as a conducting fluid and an electrical potential. The elongated DNA passes through the nanopore. Changes in current through the nanopore as a nucleotide passes through the nanopore allow identification of the nucleotide. According to one aspect, the elongated DNA passes through the nanopore as a single strand. According to this aspect, the elongated DNA may pass back and forth through the nanopore. According to one aspect, the elongated DNA passes through the nanopore as a single circularized strand. According to this aspect, the circularized strand rotates through the nanopore in first direction. The circularized strand can also rotate through the nanopore in a reverse direction.

BRIEF DESCRIPTION OF THE DRAWINGS

The foregoing and other features and advantages of the present invention will be more fully understood from the following detailed description of illustrative embodiments taken in conjunction with the accompanying drawing in which.

DETAILED DESCRIPTION

Figure 1:
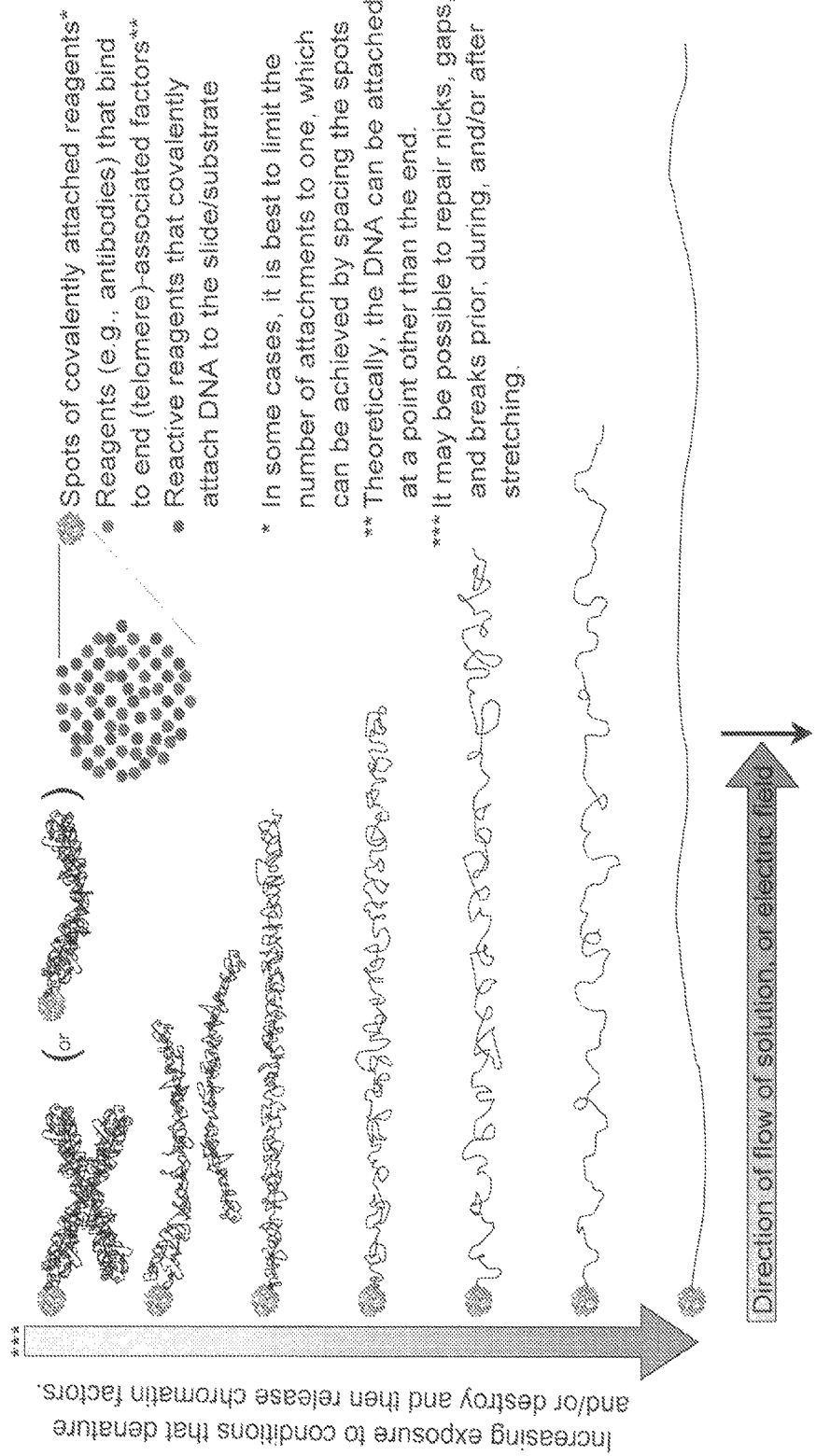
FIG. 1 is a schematic representation of aspects of the present disclosure.

The present invention is directed to methods of elongating a nucleic acid, i.e. DNA, including immobilizing or attaching the nucleic acid to a substrate. According to one aspect, the nucleic acid includes one or more factors bound thereto. The nucleic acid is contacted with at least one reagent, or subjected to one or more forces, which separates and/or removes the one or more factors from the nucleic acid. The nucleic acid is elongated as the one or more factors are removed from the nucleic acid.

According to one aspect, the present invention is directed to methods of elongating a nucleic acid, i.e. DNA, including immobilizing or attaching the nucleic acid to a substrate. According to one aspect, the nucleic acid is contacted with at least one elongation reagent which attaches to the nucleic acid in a manner to elongate the nucleic acid. Such reagents are known to those of skill in the art. For example, single stranded binding proteins are known to bind to single strands and promote untangling, i.e. straightening or elongating, of the strands.

According to one aspect, embodiments are directed to methods of elongating a chromosomal DNA including immobilizing or attaching the chromosomal DNA to a substrate. The chromosomal DNA includes one or more chromatin factors bound thereto. The chromosomal DNA is contacted with at least one reagent, or subjected to one or more forces, which removes the one or more chromatin factors from the chromosomal DNA. The chromosomal DNA is elongated as the one or more chromatin factors are removed from the DNA. According to one aspect, the present invention is directed to methods of elongating a metaphase chromosome including immobilizing or attaching the metaphase chromosome to a substrate. The metaphase chromosome includes one or more chromatin factors bound thereto. The metaphase chromosome is contacted with at least one reagent in a unidirectional fluid flow which releases or otherwise removes the one or more chromatin factors from the metaphase chromosome. The metaphase chromosome is contacted with at least one reagent in a unidirectional fluid flow which releases or otherwise removes and separates the one or more chromatin factors from the metaphase chromosome. The metaphase chromosome is contacted with at least one reagent in a unidirectional fluid flow which releases or otherwise removes and separates and carries away the one or more chromatin factors from the metaphase chromosome. The DNA of the metaphase chromosome is elongated under the influence of the unidirectional flow of the at least one reagent as the one or more chromatin factors are removed from the metaphase chromosome to produce DNA substantially lacking in chromatin factors bound thereto. According to one aspect, the DNA is long strand DNA representative of the DNA strand of the metaphase chromosome. According to one aspect, the DNA is the entire DNA strand of the metaphase chromosome.

It is to be understood from the present disclosure that the methods described herein have particular application to DNA of any source having one or more factors bound thereto and where removal of the factors is desired. The DNA need not be naturally occurring DNA. The DNA need not have all factors exemplary of naturally occurring DNA. All that is required for the present method is to begin with "starting DNA" having one or more factors bound thereto which are desired to be removed from the DNA.

The methods described herein may include a plurality of DNA immobilized or attached to the substrate and wherein the plurality of DNA is contacted with at least one reagent, or subjected to one or more forces, which removes the one or more factors from the DNA, and wherein the plurality of DNA is elongated as the one or more factors are removed from the plurality of DNA.

The methods described herein may include a plurality of DNA immobilized or attached to the substrate and wherein the plurality of DNA is contacted with two or more reagents, or subjected to one or more forces, which remove the one or more factors from the plurality of DNA, and wherein the plurality of DNA is elongated as the one or more factors are removed from the plurality of DNA.

According to one aspect, DNA referred to herein includes nucleic acids with one or more factors bound thereto. The DNA can be either single stranded or double stranded. The term DNA includes a nucleic acid, a nucleic acid molecule, a nucleic acid sequence, a nucleic acid fragment, a poly- nucleotide or an oligonucleotide which are intended to include, but are not limited to, a polymeric form of nucleotides that may have various lengths, including either deoxyribonucleotides or ribonucleotides, or analogs thereof. According to one aspect, DNA may be naturally occurring DNA or synthetic DNA. According to one aspect, DNA includes nucleic acids with factors, such as chromatin factors, bound thereto. It is to be understood that aspects of the present disclosure are directed to the removal of bound factors from DNA and that the DNA need not be chromosomal DNA, but that the methods described herein apply to any DNA where is it desirable to remove bound factors, such as those factors which may be described as chromatin factors. According to one aspect, DNA includes chromosomal DNA. According to one aspect, DNA includes metaphase chromosomal DNA. According to one aspect, DNA includes a chromosome. According to one aspect, DNA includes a metaphase chromosome.

According to one aspect, the factors bound to the DNA as described herein may include proteins (such as histone proteins), nucleic acids, RNA, nonchromosomal DNA, carbohydrates, lipids and other factors known to those of skill in the art and combinations thereof. The bound factors may be naturally occurring, i.e. bound factors commonly found in naturally occurring DNA and known to those of skill in the art, or they may result from synthetic methods involving the DNA. Accordingly, the bound factors may be synthetic factors to the extent that they are not factors known to be bound to naturally occurring DNA. Factors may become bound to synthetic DNA during methods of synthesis or processing. Accordingly, the bound factors may be synthetic factors to the extent that they are not factors known to be bound to naturally occurring DNA and have been bound to the DNA using synthetic or processing methods. According to one aspect, factors described herein are those normally associated with cellular DNA. According to one aspect, factors described herein include those commonly bound or otherwise normally associated with chromosomal DNA or chromosomes. According to one aspect, factors described herein may be referred to herein as chromatin factors. According to one aspect, the methods described herein are used to remove such factors from the DNA. According to one aspect, the methods described herein are used to remove such factors from the DNA such that substantially all of the bound or otherwise associated factors are removed from the DNA. According to one aspect, the methods described herein are used to remove such factors from the DNA resulting in DNA substantially lacking in such factors, such as chromatin factors. According to one aspect, the methods described herein are used to remove such factors from the DNA resulting in DNA having substantially no factors, such as chromatin factors, bound thereto.

According to one aspect, substrates as described herein include supports known to those of skill in the art useful for immobilizing or attaching nucleic acids using methods known to those of skill in the art "Immobilizing" refers to the nucleic acid being stably associated with the substrate surface such that it does not separate from the substrate surface under conditions of removal of bound factors. According to one aspect, the immobilized DNA includes a portion of the DNA that is free, i.e. unbound and able to move under the influence of a force. According to one aspect, the substrate includes a material having a solid surface onto which DNA is placed and immobilized, attached or otherwise bound. The solid surface may be rigid or flexible. The solid surface may be porous or nonporous. According to certain embodiments, at least one surface of the substrate will have a geometry sufficient to attached nucleic acids thereto. The substrate may be formed in essentially any shape. According to certain embodiments, at least one surface of the substrate will be planar or substantially planar. According to certain embodiments, at least one surface of the substrate will be flat or substantially flat. However, in certain embodiments, the substrate can have any surface geometry useful for attaching DNA and then contacting the DNA with one or more reagents to remove one or more factors from the DNA. Accordingly, a substrate may be a bead or the substrates may be beads. The beads may be attached or bound to a support or they may be unbound or free. In certain embodiments, the beads may be present in a fluid medium. In certain embodiments, the beads may be present in a fluid medium unbound to a support or otherwise free. In some embodiments, it may be desirable to physically separate regions of the substrate for different DNA samples with, for example, indentations, protuberances, steps, ridges, terraces, wells, channels, raised regions, etched trenches, tubes or the like. According to this aspect, DNA may be attached in wells or channels or tubes over or through which fluid may flow. The substrate may be formed from any suitable material. Exemplary substrates generally comprise planar crystalline substrates such as silica based substrates (e.g., silica, glass, quartz or the like), fused silica, silicon or crystalline substrates used in, for example, the semiconductor and microprocessor industries, such as silicon, germanium, gallium arsenide, gallium phosphide, silicon dioxide, modified silicon or the like. Additional substrate materials include glasses, ceramics, plastics, metals, alloys, carbon, agarose, cellulose, polyacrylamide, polyamide, polyimide, gelatin and other materials known to those of skill in the art. Additional substrate materials include rigid polymers such as polytetrafluoroethylene, polyvinylidenefdifluoride, polystyrene, polycarbonate, polymethylmethacrylate, polyvinylethylene, polyethyleneimine, polyoxymethylene, polyvinylphenol, polylactides, polymethacrylimide, polyalkenesulfone, polypropylene, polyethylene, polyhydroxyethylmethacrylate, polydimethylsiloxane, various block-copolymers or the like. Such substrates are generally resistant to the conditions described herein for removing bound factors from DNA. According to one aspect, the solid support can be glass or silicon. According to one aspect, the support is a planar support.

Methods of immobilizing DNA to solid supports are known in the art. DNA has been attached to beads. See for example, Dressman et al. (2003) *Proc. Natl. Acad. Sci. USA* 100:8817, Brenner et al. (2000) *Nat. Biotech.* 18:630, Albretsen et al. (1990) *Anal. Biochem.* 189:40, and Lang et al. *Nucleic Acids Res.* (1988) 16:10861. DNA has been attached to nitrocellulose. See Ranki et al. (1983) *Gene* 21:77. DNA has been attached to cellulose. See Goldkorn (1986) *Nucleic Acids Res.* 14:9171. DNA has been attached to polystyrene. See Ruth et al. (1987) Conference of Therapeutic and Diagnostic Applications of Synthetic Nucleic Acids, Cambridge U.K. DNA has been attached to teflon-acrylamide. See Duncan et al. (1988) *Anal. Biochem.* 169:104. DNA has been attached to polypropylene. See Polsky-Cynkin et al. (1985) *Clin. Chem.* 31:1438. DNA has been attached to nylon. See Van Ness et al. (1991) *Nucleic Acids Res.* 19:3345. DNA has been attached to agarose. See Polsky-Cynkin et al., *Clin. Chem.* (1985) 31:1438. DNA has been attached to sephacryl. See Langdale et al. (1985) *Gene* 36:201. DNA has been attached to latex. See Wolf et al. (1987) *Nucleic Acids Res.* 15:2911).

According to one aspect, the solid support includes attachment moieties to which nucleic acids can be attached. Such solid supports can be derivatived to include such attachment moieties or such attachment moieties can be present as part of the bulk substrate material. According to certain aspects, the nucleic acids are attached to the substrate. The attachment moieties may encompass all or a portion of the substrate. The attachment moieties may be located randomly on the surface of the substrate. The attachment moieties may be located at predetermined spacings or locations on the substrate, such as in an ordered array. According to one aspect, the attachment moieties are spaced apart sufficiently to avoid spatial interaction between adjacent DNA or chromosomes. For example, if a metaphase chromosome is attached by a telomere, the next adjacent chromosome or DNA will be separated from the metaphase chromosome by a distance longer that the longest metaphase chromosome. In this manner the adjacent chromosomes or DNA, i.e. starting chromosome or starting DNA, do not spatially interact when immobilized or attached to the substrate. The attachment moieties may be located in any desired predetermined geometric pattern or design. The attachment moieties may be the same or different. The attachment moieties may be presented as an ordered array. The attachments moieties may be selective for binding to locations on the DNA or factors or moieties bound to the DNA. For example such moieties may be one part of an antibody/antigen binding pair with the remaining part being attached to the DNA. According to one aspect, the attachment moieties may attach via telomere-associated factors. Such attachment moieties may attach to a moiety on the DNA itself. DNA may be derivatized according to methods known in the art to create a moiety on the DNA that can attach to an attachment moiety on the surface of the substrate. For example antibody-antigen pairs such as biotin-avidin may be used to bind an oligonucleotide attached to a substrate to a nucleic acid of interest such as a chromosome, such as a metaphase chromosome, such as a telomeric DNA.

As used herein, the term "attach" refers to both covalent interactions and noncovalent interactions, and mechanical interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, antibody-antigen interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell*, 3d edition, Garland Publishing, 1994. According to one aspect, metaphase chromosomes are attached to the substrate by telomeres according to methods known to those of skill in the art. For example, a nucleic acid sequence complementary to a telomere sequence of a metaphase chromosome is immobilized or attached to a substrate. The metaphase chromosome is contacted to the substrate under conditions where the telomere hybridizes to the complementary nucleic acid sequence thereby immobilizing or attaching the metaphase chromosome to the substrate. The hybridization is sufficiently stringent such that the metaphase chromosome remains immobilized or attached to the substrate under conditions that remove bound factors from the metaphase chromosome. A mechanical interaction refers to the use of mechanical or physical force to hold a nucleic acid, such as a chromosome, in place. Such a physical force can be provided by a physical structure contacting a portion of the nucleic acid and allowing the remaining portion to be free. A physical structure includes a clamp or bar for immobilizing a nucleic acid. A physical structure includes two surfaces coming together to sandwich a portion of the nucleic acid and allowing the remaining portion to be free. One or both of the surfaces may be a plane, a point, a bar or any other physical structure capable of holding DNA by physical force. According to one aspect, a physical structure such as a bar, is used to immobilize a nucleic acid, such as a chromosome, by sheer compression. Physical structures may be rigid or flexible, hard or soft, deformable or non-deformable. Force or position clamps, optical tweezers, magnetic tweezers, atomic force microscopy methods have application in the present disclosure and are described in *Current Pharmaceutical Biotechnology*, 2009, 10, 474-485 hereby incorporated by reference herein. Physical structures are particular advantageous as they are not affected by the conditions described herein (i.e., proteases, RNAses, salt, temperature changes, pH changes, etc.) to elongate nucleic acids.

According to certain aspects, the nucleic acid, DNA, chromosomal DNA, chromosome, metaphase chromosome or other state of the nucleic acid (collectively referred to as "DNA") has a first end and a second end. It is to be understood that the term "end" need not be the extreme or outermost nucleotide in a particular sequence of DNA. It is sufficient that the term "end" refer to a location along the DNA that is beyond the midpoint of the DNA in either direction. In one particular aspect the first end and the second end are located proximal to the extreme or outer most nucleotide in either direction from the midpoint of the DNA. According to certain aspects the first end of the DNA is attached to the substrate. According to certain aspects the DNA is attached to the substrate at a point intermediate to the first end and the second end. According to one aspect, the nucleic acid may be immobilized or otherwise attached to a substrate at any point along the nucleic acid including a midpoint. According to this aspect, the DNA is moveable except for the point of attachment. According to this aspect, the DNA can move about the point of attachment. The DNA can move under the influence of physical force. The DNA can move under the influence of electrical force. According to this aspect, the DNA can be carried in the direction of a force and can substantially remain in a direction or orientation while under influence of the force. However, the DNA remains attached to the substrate while under the influence of the force. The DNA remains attached to the substrate while exposed to the at least one reagent. According to certain aspects, the DNA is attached to the substrate at two locations along the DNA. According to this aspect, the two locations are distanced apart. According to this aspect, the two locations are significantly distanced apart. According to one aspect, the two locations are separated a distance of at least less than the length of the DNA.

According to one aspect, the DNA is attached to the substrate at a location at or near the first end of the DNA and at a location at or near the second end of the DNA. According to one aspect, the DNA is attached to the substrate at the first end of the DNA and at the second end of the DNA. According to a certain aspect having application herein, the points of attachment, such as two points of attachment, are located substantially horizontally on the substrate relative to a top side and bottom side of the substrate and orthogonal to a force or fluid flow. "Substantially horizontally" refers to the points of attachment being relative to one another in a non-vertical manner relative to a force or fluid flow. It is to be understood that according to this aspect, the points of attachment need only be non-vertical or substantially non vertical as the intent of a particular embodiment is to elongate the DNA under the influence of a flow of reagent in a direction substantially perpendicular to the line defining the two attachment point locations. It is to be understood that certain embodiments may utilize DNA where the two attachments point locations are substantially vertical relative to the top and bottom of the substrate. It is to be understood that certain embodiments may utilize DNA irrespective of the orientation of the two attachment points relative to each other and relative to the top and bottom of the substrate.

Once a nucleic acid including factors, such as a metaphase chromosome, is attached to a substrate. One or more reagents are contacted to the nucleic acid. The one or more reagents remove or otherwise release the factors from the nucleic acid. It is to be understood that the present disclosure contemplates that the contacting of the nucleic acid to a reagent may involve the reagent being delivered to the nucleic acid or the nucleic acid being delivered to the reagent. In the context of a metaphase chromosome, the one or more reagents are contacted to the metaphase chromosome.

According to certain aspects, the one or more reagents can be directed to or otherwise delivered to the nucleic acid on the surface of the substrate using methods and means known to those of skill in the art. For example, the reagent can be delivered to the nucleic acid by means of a tube, syringe, pipette, fluidics or any other method or means known to those of skill in the art. The reagent contacts the nucleic acid. The reagent may be delivered at a top end of the substrate and allowed to flow across the surface of the substrate to the bottom end of the substrate. According to this aspect, the reagent contacts the nucleic acid as a flow of reagent. The reagent may be delivered to the substrate as a continuous flow over a given time period. The reagent may be delivered to the substrate as several continuous flows in series over time periods. The reagent may be delivered as a unidirectional flow or stream. According to this aspect, the nucleic acid which may be a chromosome will move or tend to be pulled in the direction of the flow such as to align or substantially align with the direction of the flow as possible given the structure of the nucleic acid, which may be a chromosome. According to an embodiment where the nucleic acid is attached at a first end of the nucleic acid, the nucleic acid will be pulled and tend to straighten or align with the direction of flow of the reagent. According to an embodiment where the nucleic acid is attached at a point intermediate to the first end and the second end of the nucleic acid, the portions of the nucleic acid on either side of the attachment point will be pulled and tend to straighten or align with the direction of flow of the reagent. According to an embodiment where the nucleic acid is attached at a point near or at the first end and near or at the second end of the nucleic acid, the intermediate or middle portion of the nucleic acid will be pulled and tend to move in the direction of flow of the reagent. Since the nucleic acid is attached at or near the first end and at or near the second end, the nucleic acid will tend to curve in the direction of flow of the reagent.

According to one aspect, the nucleic acid attached to the substrate may be contacted to the reagent. According to this aspect, the nucleic acid may be delivered to the reagent. According to one aspect, the reagent may be in a vessel and the substrate with the nucleic acid may be brought into contact with the reagent in the vessel. The substrate with the nucleic acid may be submerged into the reagent. The substrate with the nucleic acid may be suspended within the reagent. According to one aspect, the substrate may be stationary while the nucleic acid contacts the reagent. According to one aspect, the substrate may be non-stationary while the nucleic acid contacts the reagent. According to this aspect, the substrate may move while the nucleic acid contacts the reagent. In this manner, the unbound portion of the nucleic acid may move as the nucleic acid contacts the reagent. According to one aspect, the substrate may be moved back and forth in the reagent. According to one aspect, the substrate may rotate in the reagent. According to one aspect, the substrate may spin in the reagent. According to one aspect, the substrate may shake in the reagent. According to the aspect where the substrate moves relative to the reagent, the reagent imparts a force on the nucleic acid.

Reagents or conditions according to the present disclosure include those known in the art capable of removing factors bound to DNA such as chromatin factors. Such reagents include salts (for example high salt concentrations), proteases (for example trypsin, serine proteases, threonine proteases, RNAses and the like. According to one aspect, the one or more reagents react with one or more factors bound to DNA to remove or release the factor from the DNA. For example, if the factor is a protein bound to the DNA, an exemplary reagent may be a protease which denatures, cleaves or destroys the protein which is then removed or released from the DNA. For example, if the factor is a RNA bound to the DNA, an exemplary reagent may be an RNAse which denatures, cleaves or destroys the RNA which is then removed or released from the DNA. Salts are also known to denature or unfold chromatin factors such that they will be released from the DNA. According to certain aspects, the DNA is contacted with two or more reagents which remove the one or more factors from the DNA. According to certain aspects, the DNA is contacted with two or more reagents in series which remove the one or more factors from the DNA.

According to an additional aspect, the nucleic acid bound to the substrate may be contacted with one or more nicking agents known to those of skill in the art. According to this aspect, the nicking agent nicks the nucleic acid in a manner to facilitate the elongation of the nucleic acid or otherwise facilitate the unwinding of the nucleic acid. The "nicked" nucleic acid may then be repaired or left in the nicked condition.

According to certain aspects, conditions under which bound factors may be removed from DNA include heat and electric field. For example, the DNA immobilized or attached to the substrate may be heated to a temperature at which proteins, RNA or other factors bound to the DNA would unfold or detach from the DNA or their respective targets associated with the DNA. Exemplary temperatures used to remove bound factors from DNA are readily apparent to those of skill in the art based on the present disclosure and include temperatures above room temperature 21° C. (68° F.) or above temperatures at which factors remain bound to DNA, such as body temperature 98.6° F. It is to be understood that the disclosure envisions temperatures above those at which factors remain bound to DNA, which can be determined by those of skill in the art for any particular DNA.

For example, the DNA immobilized or attached to the substrate may be subjected to an electric field where factors under the influence of the electric field will separate from and otherwise migrate away from the bound DNA under influence of the electric field. Suitable electric field strengths include those suitable for mobilizing chromatin factors and include those within the range of 0.01 to 20 kilo V/cm or 0.01 to 10 V/cm. One of skill in the art will recognize based on the present disclosure that pulse field electrophoresis techniques known to those of skill in the art are useful in the presently disclosed methods. According to one aspect, electric field pulses can be applied to the nucleic acid from one or more or a plurality of directions, i.e. forwards, backwards, sideways and from all angles. The direction of the electric field pulses can be altered from one to another by design or randomly so as to loosen bound factors. A useful pulse field electrophoresis method is disclosed in Schwartz D C, Cantor C R (May 1984). "Separation of yeast chromosome-sized DNAs by pulsed field gradient gel electrophoresis". *Cell* 37 (1): 67-75 hereby incorporated by reference in its entirety.

According to one aspect, the relative movement of the reagent with respect to the nucleic acid imparts a force on the nucleic acid and the bound factors. The reagent removes the one or more factors bound to the nucleic acid. According to one aspect, the relative movement of the reagent with respect to the nucleic acid causes the factors which have been removed from the nucleic acid to move away from the nucleic acid from which they have been removed. According to one exemplary embodiment, the nucleic acid, which may be a chromosome, bound to the substrate, is subjected to a flow of reagent in a direction from the point where the nucleic acid is attached to the substrate and to where the reagent flows past the nucleic acid. As the reagent flows past the nucleic acid, the factors are removed by the reagent and are then carried away from the nucleic acid as the reagent flows past and beyond the nucleic acid. According to one aspect, this embodiment can be conceptually described as "streaming" insofar as the nucleic acid is immobilized in a flowing stream of reagent. According to one exemplary embodiment, the substrate with the nucleic acid thereon, which may be a chromosome, is subjected to a flow of reagent from the first end of the substrate such as the top of the substrate, across the surface of the substrate where the nucleic acid is attached and toward the second end of the substrate such as the bottom of the substrate. The substrate may be horizontal or may be placed at an angle to facilitate flow of the reagent along the length of the substrate. As the reagent flows past the nucleic acid, the factors are removed by the reagent and are then carried away from the nucleic acid as the reagent flows past and away from the nucleic acid toward a second end of the substrate.

According to one exemplary embodiment, the substrate with the nucleic acid thereon, which may be a chromosome, is placed in whole or in part in a vessel with reagent. According to one aspect, the vessel may be a microfluidic chamber. At the very least, the nucleic acid on the substrate is contacting the reagent in the vessel. The reagent removes the factors from the nucleic acid. According to one aspect, the substrate is then removed from the vessel and reagent with the elongated nucleic acid attached to the substrate and with the factors in the reagent. According to one embodiment, the reagent may be flown or otherwise circulated through the vessel, such as with a microfluidic chamber with the substrate within the microfluidic chamber such that reagent flows into and then out of the microfluidic chamber carrying unbound factors away from the substrate and, according to one embodiment, out of the microfluidic chamber. According to one aspect, the substrate is moved within the vessel. The reagent removes the factors which are then carried away from the nucleic acid by the movement of the substrate. As an example, the substrate may be dipped into the reagent, such as repeatedly, and for a time sufficient to remove bound factors. The substrate may be moved back and forth, shaken, spun on its axis, rotated through the reagent or otherwise moved relative to the reagent. As the reagent removes the factors, the removed factors are carried away from the nucleic acid from which they were removed and into the reagent. According to one aspect, the reagent and the unbound factors may be removed from the vessel. According to one aspect, the substrate with the elongated DNA attached thereto may be removed from the vessel, for example, for further processing such as sequencing. Alternatively, the substrate with the elongated DNA attached thereto may remain in the vessel, such as a microfluidic chamber, for further processing, such as sequencing.

According to one aspect, as the factors are removed from nucleic acid, the nucleic acid may elongate. According to one aspect, as the factors are removed from nucleic acid, the nucleic acid may elongate under the influence or force of the reagent on the nucleic acid. As the factors bound to the nucleic acid are removed, the nucleic acid is able to elongate. The force of the reagent against the nucleic acid pulls the nucleic acid against its attachment point on the substrate. In this manner, elongation of the nucleic acid is facilitated. As an example, a nucleic acid is attached at its first end to a substrate. The nucleic acid is subjected to a unidirectional flow of reagent. The nucleic acid will be pulled in the direction of flow of the reagent. The reagent removes the factors bound to the nucleic acid and carries them away from the nucleic acid. As factors are removed, the nucleic acid becomes less restricted in its structure and shape. The reagent flow pulls on the nucleic acid thereby elongating the nucleic acid. According to one aspect, the reagent flow pulls on the nucleic acid thereby elongating the nucleic acid while factors are removed from the nucleic acid.

Factors may be moved away from the nucleic acid from which they were removed by methods and forces other than a flowing reagent. DNA may be elongated by methods and forces other than a flowing reagent. For example, an electric field may be used to carry unbound factors away from the DNA or otherwise assist in elongating the DNA. For example, gravity may be used to carry unbound factors away from the DNA or otherwise assist in elongating the DNA, such as when the substrate is dipped into and out of a reagent solution such that factors are removed and the weight of the DNA, when pulled out of the reagent, assists in elongating the DNA. Additional forces or conditions within the scope of the present disclosure that can be used to remove bound factors from DNA include suction, magnetism, light and the like.

According to one aspect of the method of elongation, when a nucleic acid is attached at or near a first end of the nucleic acid to the substrate, the nucleic acid is able to elongate and also change its conformation, i.e. move, such as in a twisting and turning manner, due to there being only a single attachment point. This twisting and turning is advantageous to the extent that it facilitates removal of bound factors from the DNA.

According to one aspect of the method of elongation, when a nucleic acid is attached to the substrate at or near a first end of the nucleic acid and at or near a second end of the nucleic acid, the intermediate portion of the nucleic acid is able to elongate. However, the intermediate portion of the nucleic acid maintains its conformation, such as substantially maintaining its conformation, since the intermediate portion is unable to or substantially unable to twist, turn and or otherwise alter its conformation because the nucleic acid is secured at both ends. It is to be understood that some conformational change is allowed, as factors are being released, even though the nucleic acid is attached at a first end and a second end.

According to one aspect of the method of elongation, a nucleic acid is attached to the substrate at two or more locations along the nucleic acid. According to one aspect of the method of elongation, a nucleic acid is attached to the substrate at a plurality of locations along the nucleic acid. The nucleic acid can be subjected to conditions described herein to remove bound factors. The nucleic acid with the unbound factors may then be cut at a location between the bound locations thereby creating separate DNA strands, i.e. producing separate strands, which may then be processed or analyzed such as by sequencing. According to one aspect, the breaking of the nucleic into separate strands facilitates unwinding and elongation of the nucleic acid strands. According to one aspect, the nucleic acid is attached to the substrate at two or more locations along the nucleic acid and is then cut at a location between bound locations to produce separate strands and before removing bound factors as described herein. According to this aspect, the separate strands of the DNA bound to the substrate represent ordered sequences of the original DNA strand and can be sequenced, such as being sequenced in order, such as by using the nanopore sequencing technology or other suitable sequencing technologies known to those of skill in the art and/or described herein.

According to certain aspects, the nucleic acid sequence or sequences of an entire chromosome can be separated from bound factors thereby providing a length of chromosomal DNA able to be sequenced or analyzed using methods known to those of skill in the art for sequencing nucleic acids. Accordingly, the methods described herein provide chromosomal DNA unhindered or uninhibited by factors which constrain or conform the chromosomal DNA into a configuration which makes sequencing and analysis difficult. By using the methods described herein, the chromosomal DNA can be "cleaned" of chromatin factors and the chromosomal DNA can be elongated, removed from the substrate and isolated for further study.

According to certain aspects, the elongated nucleic acids produced by the methods described may be amplified, sequenced and/or analyzed. According to certain aspects, chromosomal DNA resulting from the methods described herein may be sequenced and analyzed. The DNA produced by the methods described herein may be sequenced and analyzed using methods known to those of skill in the art.

In various embodiments, the methods disclosed herein include amplification of the elongated nucleic acids, such as elongated chromosomal DNA. Amplification methods may comprise contacting a nucleic acid with one or more primers that specifically hybridize to the nucleic acid under conditions that facilitate hybridization and chain extension. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self-sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:

7790), the amplification methods described in U.S. Pat. Nos. 6,391,544, 6,365,375, 6,294,323, 6,261,797, 6,124,090 and 5,612,199, or any other nucleic acid amplification method using techniques well known to those of skill in the art. In exemplary embodiments, the methods disclosed herein utilize PCR amplification.

In certain exemplary embodiments, methods for amplifying nucleic acid sequences are provided. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self-sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach and PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research*, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.*, 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., *Biotechniques*, 26:112-126 (1999); Becker-Andre et al., *Nucleic Acids Research*, 17:9437-9447 (1989); Zimmerman et al., *Biotechniques*, 21:268-279 (1996); Diviacco et al., *Gene*, 122:3013-3020 (1992); Becker-Andre et al., *Nucleic Acids Research*, 17:9437-9446 (1989); and the like.

In certain embodiments, methods of determining the sequence of one or more nucleic acid sequences of interest resulting from the methods described herein are provided. Determination of the sequence of a nucleic acid sequence of interest can be performed using a variety of sequencing methods known in the art including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (Porreca et al (2007) *Nat. Methods* 4:931), polymerized colony (POLONY) sequencing (U.S. Pat. Nos. 6,432,360, 6,485,944 and 6,511,803, and PCT/US05/06425); nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., on cyclic array sequencing using platforms such as Roche 454, Illumina Solexa, AB-SOLiD, Helicos, Polonator platforms and the like, can also be utilized. A variety of light-based sequencing technologies are known in the art (Landegren et al. (1998) *Genome Res.* 8:769-76; Kwok (2000) *Pharmocogenomics* 1:95-100; and Shi (2001) *Clin. Chem.* 47:164-172).

According to one aspect, the elongated DNA can be sequenced by nanopore sequencing technology. Nanopore sequencing includes a method of determining the components of a polymer, such as a polynucleotide, based upon interaction of the polymer with the nanopore. Likewise, nanopore technology can be used to identify nonnucleic acid moieties associated with the elongated DNA, such as factors which may remain bound to the elongated DNA. Nanopore sequencing may be achieved by measuring a change in the conductance of ions through a nanopore that occurs when the size of the opening is altered by interaction with the polymer. According to certain aspects, methods of moving a nucleic acid toward and through a nanopore are known to those of skill in the art. For example, electrophoresis may be used to direct a nucleic acid toward and through a nanopore. Enzymes attached to the nanopore may be used to guide a nucleic acid through a nanopore. As each nucleotide moves through the nanopore, the nucleotide obstructs the nanopore to a different degree that is characteristics of the nucleotide. The amount of current that can pass through the nanopore varies with the type of nucleotide passing through the nanopore, i.e. whether A, C, G, T or other modified nucleotide. The change in current through the nanopore represents a direct reading of the nucleotide passing through the nanopore, and accordingly the nucleic acid passing through the nanopore. According to this aspect, the nucleotides of a nucleic acid may be identified in general or in sequence.

Nanopores suitable for nanopore sequencing methods are known to those of skill in the art and include a hole or passage through a membrane formed by a multimeric protein ring. The width of a typical nanopore for purposes of sequencing is about 0.2 to about 25 nm. Representative nanopores include alpha-hemolysin (αHL) and *Mycobacterium smegmatis* porin A (MspA). According to one aspect, the method includes passing an elongated DNA through a nanopore under the influence of an electric potential and determining the identity of a nucleotide passing through the nanopore based on the change in electric current as the nucleotide passes through the nanopore. According to one aspect, the method includes (a) providing two separate pools of liquid containing electrically conducive medium and a nanopore-perforated interface between the two pools, where the interface contains a nanopore; (b) providing elongated candidate polynucleotide molecules in one of the pools; (c) applying a voltage differential across the pools; and (d) making interface-dependent measurements of ionic current over time as individual nucleotides of a single elongated polynucleotide interact sequentially with the interface, yielding data suitable to determine a nucleotide-dependent characteristic of the polynucleotide. In a related aspect, the interface is a membrane.

Nanopores, as used herein, include transmembrane structures that may permit the passage of molecules through a membrane. A multimeric nanopore may include any number of subunits (such as 1, 2, 3, 4, 5, 6, 7, 8, 9, or 10 other nanopore subunits). Examples of nanopores include α-hemolysin (*Staphylococcus aureus*) and MspA (*Mycobacterium smegmatis*). Examples of nanopores may be found in the art describing nanopore sequencing or described in the art as pore-forming toxins, such as the β-PFTs Panton-Valentine leukocidin S, aerolysin, and Clostridial Epsilon-toxin, the α-PFTs cytolysin A, the binary PFT anthrax toxin, or others such as pneumolysin or gramicidin. Synthetic nanopores are also known in the art. See "Embedding a Carbon Nanotube Across the Diameter of a Solid State Nanopore," J. Vac. Sci. Technol. 29 (5).

Methods for nanopore sequencing are known in the art, for example, as described in U.S. Pat. No. 5,795,782, *Proc. Natl. Acad. Sci. USA* 93 (24): 13770-3, *Sci. Am.* 294 (1): 46-54, and *Nature Nanotechnology* 4 (4): 265-270, each of which are hereby incorporated by reference in their entireties. One embodiment of nanopore sequencing involves a nanopore-perforated membrane immersed in a voltage-conducting fluid. A voltage is applied across the membrane, and an electric current results from the conduction of ions through the nanopore. When the nanopore interacts with polymers, such as DNA, flow through the nanopore is modulated in a monomer-specific manner, resulting in a change in the current that permits identification of the monomer(s).

Methods of passing nucleic acids through nanopores are known. For example, a DNA polymerase may be used to ratchet a DNA substrate through the nanopore. In some embodiments, the polymerase is phi29 DNA polymerase, T7 DNA polymerase, Klenow fragment of DNA polymerase 1, or other DNA polymerase. In other embodiments, passive approaches can be used to slow the movement of DNA through a nanopore. These approaches may include nucleotide labeling, end termination of ssDNA with DNA hairpins, the use of positively charged residues in the nanopore as molecular brakes, and modification of pore shape to optimize processivity.

In some embodiments, the membrane of the nanopore sequencing technique is lipid bilayer. In some embodiments, the membrane of the nanopore sequencing technique is an artificial membrane, composed of a material such as $Al_2O_3$, $TiO_2$, $HfO_2$, $SiO_2$, SiN, or grapheme.

The various embodiments of the fusion nanopore may be employed in the sequencing of single-stranded or double-stranded DNA, cDNA, RNA, mRNA, tRNA, rRNA, micro-RNA, siRNA, or any polynucleotide, as well as other polymers including but not limited to polypeptides.

Methods of fluorescence sequencing using nanopores are known and include those described in "Optical Recognition of Converted DNA Nucleotides for Single Molecule DNA Sequencing Using Nanopore Arrays," Nano Left. 10 (6): 2237-2244, and "Synchronous Optical and Electrical Detection of Biomolecules Traversing Through Solid-State Nanopores," Rev. Sci, Instrum. 81.

According to one aspect of the present disclosure, the use of elongated DNA as described herein is particularly advantageous with sequencing methods including nanopore sequencing as the bound factors are removed from DNA and so do not hinder sequencing efforts, especially with nanopore sequencing methods. According to this aspect, the nucleotide of elongated DNA lacks bound factors that can affect changes in electrical current as the nucleotide passes through the nanopore. The result is that sequencing efforts using nanopore technology and elongated DNA are more accurate because the nucleotide passing through the DNA is unhindered by bound factors giving a more uniform current change that is more representative of the particular nucleotide passing through the nanopore.

This invention is further illustrated by the following example, which should not be construed as limiting. The contents of all references, patents and published patent applications cited throughout this application are hereby incorporated by reference in their entirety for all purposes.

Example I

Methods of isolating a metaphase chromosome, and other relevant methods and conditions, are known to those of skill in the art and include those described in Rasmussen et al., Lab Chip, 2011, 11, 1431-1433 (2011) and Bauer et al., *Nucleic Acids Research,* 2012, 1-7 (doi:10.1093/nar/gks931) each of which is hereby incorporated by reference in its entirety.

Example II

One exemplary embodiment of a method of attaching a metaphase chromosome to a substrate is provided as follows. A substrate includes one or more covalently attached olignucleotides the free ends of which are complementary to respective telomeric sequences. One or more telomeric sequences are contacted to the substrate under condition where the one or more oligonucleotides hybridize to corresponding telomeric sequences. According to an alternate embodiment, the free end of an attached oligonucleotide may include a moiety that can be covalently attached to a telomeric sequence. The moiety can be chemically activated to become covalently attached to the telomeric sequence, and accordingly, activation of the moiety will allow covalent attachment of the telomeric sequence and accordingly the chromosomal DNA to the substrate. According to one aspect, the metaphase chromosome may be denatured via heat, salt, alkaline conditions, or the like sufficient to promote either hybridization to the covalently attached oligonucleotide or covalent attachment to the covalently attached oligonucleotide. According to an alternate aspect, the covalently attached oligonucleotide may include one or more locked nucleic acids as known in the art to enhance hybridization of the oligonucleotide to the telomeric sequence. According to an alternate aspect, the covalently attached oligonucleotide may be RNA or DNA. According to one aspect, RNA hybridized to telomeric DNA may be suitably stable for purposes of the present disclosure. According to an additional aspect, the covalently attached oligonucleotide may be RNA complementary to RNA located at the telomere. In this manner, the telomeric RNA would hybridize to the covalently attached oligonucleotide. Optionally, the covalently attached RNA would then be covalently attached to the telomeric DNA. Other methods of enhancing hybridization of complementary nucleic acids are known to those of skill in the art.

One exemplary embodiment of a method of attaching a metaphase chromosome to a substrate is provided as follows. The substrate includes one or more antibodies covalently attached thereto. The antibodies are directed against proteins or other factors that are associated with or otherwise located at the telomere of a metaphase chromosome. In this manner the metaphase chromosome would be immobilized to or otherwise attached to the substrate via antibody-antigen binding. According to an alternate aspect, an antibody could be used with an oligonucleotide complementary to telomeric DNA. In this manner, the antibody would bind the telomere and the oligonucleotide would hybridize to the telomeric DNA.

One exemplary embodiment of a method of attaching a metaphase chromosome to a substrate is provided as follows. The substrate includes one or more antibodies covalently attached thereto. The antibodies are directed against proteins or other factors that are associated with or otherwise located at the telomere of a metaphase chromosome. In this manner the metaphase chromosome would be immobilized to or otherwise attached to the substrate via antibody-antigen binding. In addition, the antibody includes a moiety attached thereto that can covalently bind to a nucleic acid, such as a telomeric sequence. The moiety can be chemically activated to become covalently attached to the telomeric sequence, and accordingly, activation of the moiety will allow covalent attachment of the telomeric sequence and accordingly the chromosomal DNA to the substrate.

According to one exemplary aspect, the attachment force, mechanism or chemistry used to attach the DNA to a substrate is resistant to the conditions used to remove bound factors and otherwise elongate the DNA.

Example III

A method of removing chromatin factors and elongating a nucleic acid is provided with reference to FIG. 1. As shown in FIG. 1, a chromosome or a segment of DNA is attached via one end to a surface, such as that of a glass slide. The attachment is made possible via spots on the surface that contain a) reagents that recognize proteins/factors that are associated with the end of a chromosome/DNA and bind thereto and b) reagents that can covalently attach DNA to the surface or can be activated to covalently attach DNA to the surface. The surface can be manipulatable. Known ligand-ligand binding pairs can also be used to attach a chromosome/DNA with one ligand attached to the substrate and its binding pair attached to the chromosome/DNA using methods known to those of skill in the art. The chromosome/DNA may be attached at more than one spot on the substrate surface and not necessarily by its end. However, one exemplary embodiment is to attach the chromosome/DNA by one end only as a single attachment point. This can be achieved by, for example, targeting the ends of the chromosome/DNA for attachment and spacing the spots such that no chromosome/DNA can be attached at two points.

After attachment, the surface is exposed to a stream of solution or liquid medium and/or electric field that moves in one direction relative to the substrate. Reagents (such as proteases, salts, etc.) are then added to the stream so that the factors, such as those found in chromatin, are gently denatured and/or destroyed and then released and removed away from the chromosome/DNA. As a consequence, the DNA will be extended or elongated. The DNA can then be attached to the surface for subsequent analysis by FISH or in situ sequencing or otherwise subject to analysis, amplification, sequencing, etc.

Chromosomal DNA may contain single-strand nicks and single-strand gaps. Nicks or gaps may be subject to ligations with or without fill-in polymerization before, during, or after the stretching or elongation of the chromosome/DNA. Chromosomal DNA may also have double-strand breaks or double-strand gaps. Double-strand breaks or double-strand gaps may be repaired using methods known to those of skill in the art, depending on the nature of the breaks and gaps and how closely the ends are held to each other, with success most likely if repair were attempted prior to extensive disruption of the chromatin factors holding the ends together.

Observation of the gradual stretching of a chromosome or other factor-bound DNA has the potential to reveal packing/organizational features of the chromosome or factor-bound DNA. Observation methods are known to those of skill in the art and will be readily identifiable based on the present disclosure. Use of different conditions to remove factors could further reveal packing/organizational features.

Example IV

Figure 2:
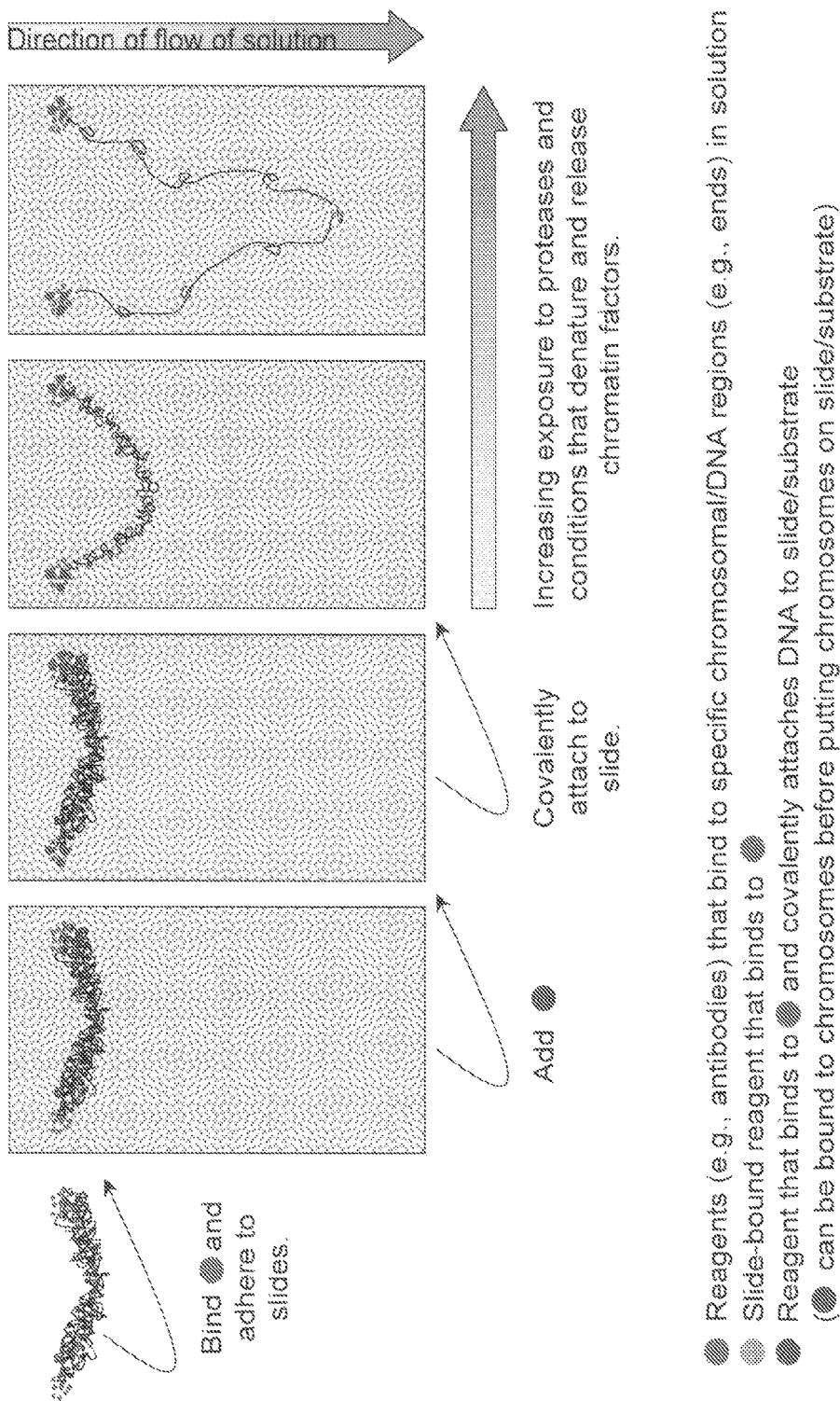
FIG. 2 is a schematic representation of aspects of the present disclosure.

A method of removing chromatin factors and elongating a nucleic acid is provided with reference to FIG. 2. As shown in FIG. 2, a chromosome or a segment of DNA is attached to a surface, such as that of a glass slide by points at or near the ends of the chromosome or segment of DNA. The attachment is made possible via spots on the surface that contain a) reagents that recognize proteins/factors that are associated with the end of a chromosome/DNA and bind thereto and b) reagents that can covalently attach DNA to the surface or can be activated to covalently attach DNA to the surface. The surface may be manipulatable. Known ligand-ligand binding pairs can also be used to attach a chromosome/DNA with one ligand attached to the substrate and its binding pair attached to the chromosome/DNA using methods known to those of skill in the art.

After attachment, the surface is exposed to a stream of solution or liquid medium and/or electric field that moves in one direction relative to the substrate. Reagents (such as proteases, salts, etc.) are then added to the stream so that the factors, such as those found in chromatin, are gently denatured and/or destroyed and then released and removed away from the chromosome/DNA.

As a consequence, the DNA will be extended such that the conformational changes of the chromosome/DNA caused by release of factors from the chromosome/DNA lying between the two attached points can be recorded and used to deduce the original packaging/organizational features of the chromosome/DNA. The DNA can then be attached to the surface for subsequent analysis by FISH or in situ sequencing or otherwise subject to analysis, amplification, sequencing, etc.

EQUIVALENTS

Other embodiments will be evident to those of skill in the art. It should be understood that the foregoing description is provided for clarity only and is merely exemplary. The spirit and scope of the present invention are not limited to the above example, but are encompassed by the claims. All publications, patents and patent applications cited above are incorporated by reference herein in their entirety for all purposes to the same extent as if each individual publication or patent application were specifically indicated to be so incorporated by reference.

What is claimed is:

1. A method of sequencing elongated DNA comprising
   attaching DNA to a substrate by one or more covalent bonds, an antibody interaction, a ligand-ligand interaction, or a telomere-associated factor, wherein the DNA includes one or more factors bound thereto,
   contacting the DNA with at least one reagent which removes the one or more factors from the DNA,
   elongating the DNA as the one or more factors are removed from the DNA,
   passing elongated DNA through a nanopore under an electrical potential,
   measuring a change in current resulting from a nucleotide of the elongated DNA passing through the nanopore, and
   identifying the nucleotide based on the change in current.

2. The method of claim 1 wherein the elongated DNA is passed through the nanopore in a back and forth direction.

3. The method of claim 1 wherein the elongated DNA is circular elongated DNA.

4. The method of claim 3 wherein the circular elongated DNA is rotated through the nanopore.

5. The method of claim 3 wherein the circular elongated DNA is continuously rotated through the nanopore.

6. The method of claim 3 wherein the circular elongated DNA is revolved through the nanopore.

7. The method of claim 3 wherein the circular elongated DNA is continuously revolved through the nanopore.

8. The method of claim 3 wherein the circular elongated DNA spins through the nanopore.

9. The method of claim 3 wherein the circular elongated DNA continuously spins through the nanopore.

10. The method of claim 1 wherein the one or more factors includes a protein, RNA, carbohydrate, lipid or nonchromosomal DNA.

11. The method of claim 1 wherein the one or more factors are one or more chromatin factors.

12. The method of claim 1 wherein the DNA is double stranded DNA, single stranded DNA, or chromosomal DNA.

13. The method of claim 1 wherein the DNA has a first end and a second end and wherein the first end of the DNA is attached to the substrate.

14. The method of claim 1 wherein the DNA is elongated under influence of a flowing reagent.

15. The method of claim 1 wherein the DNA is elongated under influence of an electric field.

16. The method of claim 1 wherein the DNA is elongated under influence of gravity.

17. The method of claim 1 wherein the DNA has a first end and a second end and wherein the DNA is attached to the substrate at the first end and the second end.

18. The method of claim 1 wherein the DNA has a first end and a second end and wherein the DNA is attached to the substrate at the first end and the second end and wherein the first end and second end are separated a distance of at least less than the length of the DNA.

19. The method of claim 1 wherein the DNA has a first end and a second end and wherein the DNA is attached to the substrate at a location intermediate the first end and the second end.

20. The method of claim 1 wherein the DNA has a first end and a second end and the first end of the DNA is attached to the substrate, wherein the at least one reagent is flowed from a first end of the DNA to a second end of the DNA.

21. The method of claim 1 wherein the DNA has a first end and a second end and the first end of the DNA is attached to the substrate, wherein the at least one reagent is flowed from a first end of the DNA to a second end of the DNA whereby factors are removed from the DNA by the at least one reagent and the DNA is elongated under the influence of the flowing reagent.

22. The method of claim 1 wherein the DNA has a first end and a second end and the first end of the DNA is attached to the substrate, wherein the at least one reagent is flowed one or more times from a first end of the DNA to a second end of the DNA.

23. The method of claim 1 wherein the DNA has a first end and a second end and the first end of the DNA is attached to the substrate, wherein the at least one reagent is flowed one or more times from a first end of the DNA to a second end of the DNA whereby factors are removed from the DNA by the at least one reagent and the DNA is elongated under the influence of the flowing reagent.

24. The method of claim 1 wherein the DNA is contacted with two or more reagents which remove the one or more factors from the DNA.

25. The method of claim 1 wherein the DNA is contacted with two or more reagents in series which remove the one or more factors from the DNA.

26. The method of claim 1 including a plurality of DNA attached to the substrate and wherein the plurality of DNA is contacted with at least one reagent which removes the one or more factors from the DNA, and wherein the plurality of DNA is elongated as the one or more factors are removed from the plurality of DNA.

27. The method of claim 1 including a plurality of DNA attached to the substrate and wherein the plurality of DNA is contacted with two or more reagents which remove the one or more factors from the plurality of DNA, and wherein the plurality of DNA is elongated as the one or more factors are removed from the plurality of DNA.

28. The method of claim 1 wherein the substrate is a planar substrate.

29. The method of claim 1 wherein the substrate is a planar substrate and wherein the at least one reagent flows across the surface of the planar substrate to remove the one or more factors from the DNA and to elongate the DNA.

30. The method of claim 1 wherein the substrate is a planar substrate, wherein the DNA has a first end and a second end and the first end of the DNA is attached to the planar substrate and wherein the at least one reagent flows across the surface of the planar substrate from the first end of the DNA to the second end of the DNA to remove the one or more factors from the DNA and to elongate the DNA.

31. The method of claim 1 wherein the substrate is a planar substrate including a plurality of DNA having a first end and a second end and being attached to the substrate at the first end and wherein the at least one reagent flows across the surface of the planar substrate from the first end of the DNA to the second end of the DNA to remove the one or more factors from the plurality of DNA and to elongate the plurality of DNA.

\* \* \* \* \*